United States Patent
Kozak et al.

(10) Patent No.: US 6,517,840 B1
(45) Date of Patent: Feb. 11, 2003

(54) PRODUCTION OF A PRODUCT ENRICHED IN ISOFLAVONE VALUES FROM NATURAL SOURCES

(75) Inventors: William G. Kozak, Hatfield, PA (US); Puvin Pichai, Collegeville, PA (US); Patricia J. Voorstad, Limerick, PA (US); Sang I. Kang, Loveland, OH (US); Michael Rueter, Plymouth Township, PA (US); Jonathan D. Thomas, Philadelphia, PA (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/453,769

(22) Filed: Dec. 2, 1999

Related U.S. Application Data

(60) Provisional application No. 60/110,604, filed on Dec. 2, 1998.

(51) Int. Cl.[7] .......................... A01N 65/00; A61K 35/78
(52) U.S. Cl. .................... 424/195.1; 536/128; 549/403; 426/634
(58) Field of Search .................. 536/128; 549/403; 424/195.1; 426/634

(56) References Cited

U.S. PATENT DOCUMENTS

| | | |
|---|---|---|
| 3,864,362 A | 2/1975 | Feuer et al. |
| 4,428,876 A | 1/1984 | Iwamura |
| 5,141,746 A * | 8/1992 | Fleury et al. ............ 424/195.1 |
| 5,320,949 A | 6/1994 | Shen |
| 5,352,384 A | 10/1994 | Shen |
| 5,424,331 A | 6/1995 | Shlyankevich |
| 5,523,087 A | 6/1996 | Shlyankevich |
| 5,554,514 A | 9/1996 | Revel et al. |
| 5,554,519 A * | 9/1996 | Weber et al. ............... 435/125 |
| 5,569,459 A | 10/1996 | Shlyankevich |
| 5,637,561 A | 6/1997 | Shen et al. |
| 5,637,562 A | 6/1997 | Shen et al. |
| 5,670,632 A | 9/1997 | Chaiborsky |
| 5,679,806 A | 10/1997 | Zheng et al. |
| 5,702,752 A | 12/1997 | Gugger et al. |
| 5,726,034 A * | 3/1998 | Bryan et al. ............... 435/68.1 |
| 5,821,361 A | 10/1998 | Waggle et al. |
| 5,885,632 A | 3/1999 | Takebe et al. |

FOREIGN PATENT DOCUMENTS

| | | |
|---|---|---|
| CH | 626 359 A | 11/1981 |
| EP | 0129667 | 1/1985 |
| EP | 0135172 | 3/1985 |
| EP | 0 795 553 A1 | 9/1997 |
| GB | 1195050 A | 6/1970 |
| JP | 1247396 | 11/1986 |
| JP | 5170756 | 7/1993 |
| JP | 5176756 | 7/1993 |
| JP | 2000281673 | * 10/2000 |
| WO | WO 98/49153 A | 11/1998 |

OTHER PUBLICATIONS

S. Barnes et al. Isoflavones and their conjugates in soy foods: Extraction conditions and analysis by HPLC–Mass Spectrometry. J. Agric. Food Chem. 1994,42,2466–2474.*

Cheng et al., *Estrogenic Activity of Some Naturally Occuring Isoflavones*, Annals of New York Academy of Sciences, vol. 61; pp. 652–654, 1955.

*Effect of Genistein on the Fertility of Mice*, J. Endocrinology, vol. 13, 94–100, Oct. 1955.

Barnes et al., *Isoflavones and Their Conjugates in Soy Foods: Extraction Conditions and Analysis by HPLC–Mass Spectrometry*, J. Agric. Food Chem. 1994, vol. 42, No. 11, pp. 2466–2474.

* cited by examiner

Primary Examiner—Samuel Barts
Assistant Examiner—Devesh Khare
(74) Attorney, Agent, or Firm—John E. Drach; Daniel S. Ortiz; Aaron R. Ettelman

(57) ABSTRACT

A process for recovering isoflavone values from a biomass in which the isoflavone values are extracted from the biomass with a selective solvent for the isoflavone values, solid isoflavone values and the selective solvent are contacted with a nonsolvent or antisolvent for the isoflavone value which is miscible with the selective solvent. Optionally the nonsolvent or antisolvent is admixed with water during the contact with the solid isoflavone values to improve the purity and recovery of the solid isoflavone values.

28 Claims, 8 Drawing Sheets

F I G. I

Water Addition in Hexane Wash Step

Effectiveness of Water Addition to Hexane Wash for ISFV Purification

- ◆ Single Hexane Wash
- ■ With Secondary Hexane Wash

X-axis: % Water in Hexane/Evap Slurry Mixture
Y-axis: ISFV Purity (%) in Final Product

FIG. 9

PRODUCTION OF A PRODUCT ENRICHED IN ISOFLAVONE VALUES FROM NATURAL SOURCES

CROSS-REFERENCE TO RELATED APPLICATIONS

This application claims the priority of Provisional Application 60/110,604, filed Dec. 2, 1998, the contents of which are incorporated herein by reference.

FEDERALLY SPONSORED RESEARCH AND DEVELOPMENT

This invention was not developed and is not related to any federally sponsored research and development.

FIELD OF THE INVENTION

The invention relates to a process for the production of a composition enriched in isoflavone values by treatment of a biomass containing the isoflavone values.

BACKGROUND OF THE INVENTION

Isoflavones are a unique class of plant flavonoids that have a limited distribution in plants and can be described as aromatic ketones. The isoflavones in the plant sources are generally in the glycosolated form.

Recently the health benefits of the isoflavones have been investigated and a favorable portrait of the physiological and health benefits associated with isoflavones has been published in the press and the literature.

Some of the references to physiological health effects include Cheng et al., Estrogenic Activity of Some Naturally Occurring Isoflavones, Annals of the New York Academy of Sciences, Vol. 61; Pages 652–654; Catabolic Activity of Isoflavones U.S. Pat. No. 3,864,362, Feb. 4, 1975; Prevention of Osteoporosis, U.S. Pat. No. 5,424,331, Jun. 13, 1995; Treatment of Diabetic Male Sexual Dysfunction, U.S. Pat. No. 5,523,087, Jun. 4, 1996; Management of Premenstrual Syndrome, U.S. Pat. No. 5,569,459, Oct. 29, 1996; Treatment of Menopausal and Premenstrual Symptoms, U.S. Pat. No. 5,498,631, Mar. 12, 1996; Compounds and Pharmaceutical Compositions for the Treatment of Hypoovarianism, EP 0 129,667, A1 published Jan. 2, 1985; Method for Treatment of Osteoporosis, EP 0 135,172 A2, published Mar. 27, 1985: Fast, June; the Effect of Genistein on the Fertility of Mice, J. Endocrinology, Vol. 13, 94–100, October, 1955; Food for Controlling Cancer, Bone Disease or Immunity Obtained by Fermenting Pulses esp. Soy Beans, Hydrolyzing Protein and Forming Aglycone of Isoflavone Glycoside, U.S. Pat. No. 5,885,632, Mar. 22, 1994; Estrogenic, antioxidant, antihaemolytic, antibacterial, anti-hyperlipidemic, anti-hypercholesterolemic and anti-cancer activity are disclosed in JP 5170756, Sep. 7, 1993.

The isoflavones are generally present in plant substrates in relatively low concentrations. It is desirable to provide isoflavones in a higher concentration so that they can be utilized as a dietary supplement to provide enhanced levels of isoflavones without consumption of substantial amounts of the natural products from which the isoflavones are derived.

A particularly good source of isoflavone values have been materials derived from soybeans, however isoflavones values are also present in substantial amounts in plants such as red clover.

U.S. Pat. No. 5,554,519 discloses a method for preparing genistein by fermentation and recovering the genistein from the fermentation broth by extraction with a water immiscible organic solvent at a pH of from about 8 to about 11. Solvents such as ethyl acetate, amyl acetate, chloroform, ethylene dichloride, ethers, ketones, and alcohols, the preferred solvents include n-butanol, amnyl acetate and ethyl acetate. The genistein is recovered from a dilute aqueous solution of carbohydrates and proteins. Genistein is the only isoflavone present so there is no concern with extracting other isoflavones from the fermentation medium.

U.S. Pat. Nos. 5,320,949, 5,352,384, 5,637,561, and 5,637,562 disclose methods for preparing aglucone isoflavone enriched soy products. The glucone isoflavones are extracted from the soy starting material with an aqueous extractant to extract protein and glucone isoflavones, the extract is treated with a glucosidase to convert gluronc isoflavoaes to aglucone isoflavones and the pH adjusted to precipitate the aglacone isoflavanes which are recovered with the soy material. The process provides a soy product enriched in aglucone isoflavone.

U.S. Pat. No. 5,670,632 discloses a method for recovering isoflavones from a soy extract. The soy extract at a pH of about 9 is treated by a solids separation means to remove suspended solids. The solution less the solids is contacted with a highly polar cationic exchange resin and the isoflavone values are desorbed from the polar resin by an acidic aqueous alkanol containing 1–3 carbon atoms. The isoflavone values are recovered from the solvent.

U.S. Pat. No. 5,679,806 discloses a process for isolation and purification of isoflavones from biomass sources. The biomass is extracted with a solvent to provide a crude extract. The preferred solvent is alcohol. The crude extract is diluted with water and contacted with a reverse phase matrix in a column to adsorb the isoflavone values and the isoflavone values are desorbed and eluted in fractions from the reverse phase matrix. The individual isoflavones recovered from the reverse phase matrix in the absorbent column can be further purified.

U.S. Pat. No. 5,702,752 discloses a process for recovering isoflavone values from a soy molasses feed stream, in particular, the recovery of genistein. An aqueous soy extract is subjected to ultrafiltration to recover isoflavones as a permeate and the isoflavones further purified to recover isoflavones in high concentration.

U.S. Pat. No. 5,821,361 discloses a method for recovering isoflavones from soy molasses. A solution of soy molasses in water is treated at a pH and temperature to convert isoflavone conjugata to isoflavone glucosides, precipitating the isoflavone glucosides and separating the isoflavone glucosides from the solution by mechanical means such a filtration, centrifugation and the like. Recovering the solids comprising isoflavone glucosides.

U.S. Pat. No. 4,428,876 is directed to a process for isolating saponins and flavonoids from leguminous plants. The plant material is extracted with a dilute aqueous alkaline solution, the insoluble material is separated from the extract and the saponins and flavonoids are recovered by adsorption in a slightly polar adsorbent resin and eluted with a polar solvent.

JP 05176756A discloses recovery of isoflavone derivatives from soy based materials by extracting the soy based material with 80% methanol. The extract was filtered and evaporated to produce a solid. The solid was dissolved in ethanol and the isoflavone derivatives recovered by adsorption in an adsorption resin, eluted with 80% ethanol and the material dried to provide a composition containing at least 90% isoflavone derivatives.

JP 61247396A discloses a method from preparing genistein by fermentation, separating the solids from the aqueous phase, extracting the aqueous phase with an organic solvent and recovering the genistein from the solvent by adsorption and elution from an adsorption resin bed.

BRIEF DESCRIPTION OF THE INVENTION

The process of the present invention comprises extracting isoflavone values from plant material and recovering the isoflavone values from the extracting solvent. The solvent is a composition which has an affinity for the isoflavone values in the plant material. Preferably the solvent has a higher affinity and is selective for the isoflavone values over the other substituents in the plant material. The extraction separates the isoflavone values from a portion of the other materials in the plant material.

The isoflavone values are recovered from the solvent preferably by a method that further purifies the recovered isoflavone values. The isoflavone values can be recovered from the solvent by methods such as evaporation, precipitation, and crystallization and contact or washing with a nonsolvent or antisolvent for the isoflavone values. Fine particles of the isoflavone values, which can be formed in the washing step, are difficult to recover due to the small particle size. The small isoflavone particles can be agglomerated by addition of small amounts of water to a slurry of the isoflavone values in a nonsolvent for the isoflavone values and can then be readily separated from the solvent.

The purity of the isoflavone values recovered from the plant materials is dependent upon the nature of the solvent utilized, and the steps of recovering the isoflavone values from the solvent extract.

BRIEF DESCRIPTION OF THE DRAWINGS

FIG. 9 is a plot of isoflavone product purity vs. the amount of water in the nonsolvent for the isoflavone values in the contacting or washing step of the process.

DETAILED DESCRIPTION OF THE INVENTION

Figure 1:
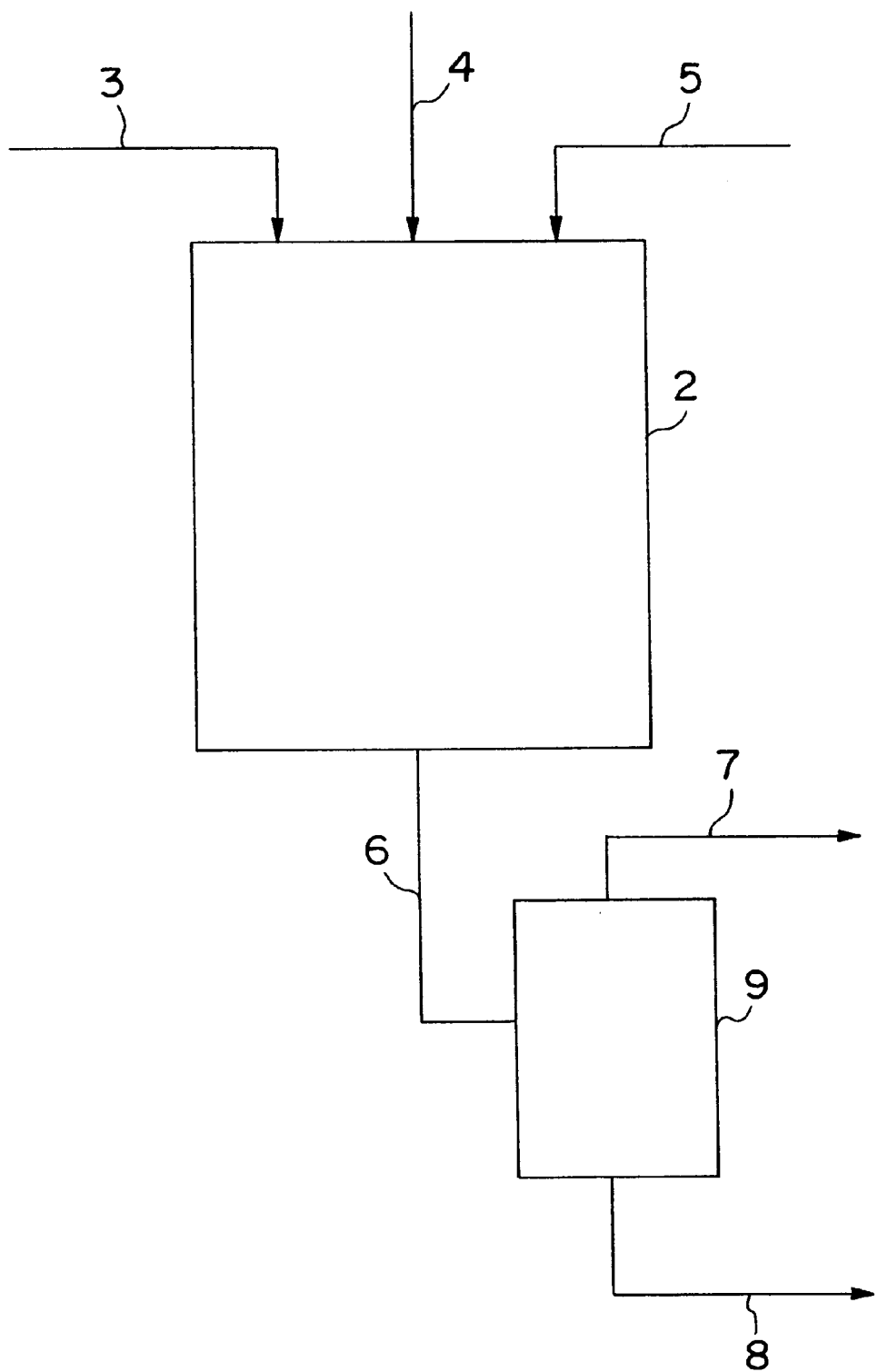
FIG. 1 is a diagrammatic representation of a mixing-extraction-separation zone which can be operated on a continuous or batch basis.

The plant material which is useful for the process of the present invention comprises a biomass which contains the isoflavone values. At the present time, due to its abundance and ready availability, plant materials derived from soybeans are the preferred feed for use in the process of the present invention. Materials such as condensed soy solubles (hereinafter CSS, also known as soy molasses) and extracts of defatted soybean meal or flour and red clover extracts are useful as the feed to the process. The nature of the solvent utilized is dependent upon the nature of the plant material and the impurities present in the starting material and the presence of substantial amounts of water. The solvent is not miscible with water and is selective for the isoflavone values over impurities in the biomass.

When CSS is utilized as the starting material for the process of the present invention, since it is a water dispersible, viscous composition, for ease of extraction, CSS is generally mixed with water and the isoflavone values are extracted from the mixture of water and undissolved solids with a solvent for the isoflavone values which is not miscible or only sparingly soluble in water. Solvents such as low molecular weight fatty acid esters such as ethyl acetate, propyl acetate, butyl acetate, amyl acetate and cyclohexanol have been found to be suitable solvents useful in the practice of the invention. Other water immiscible or slightly soluble compounds such as the higher alcohols such as butyl alcohol, amyl alcohol and the like and water immiscible ketones, water immiscible aldehydes and other water immiscible or slightly water soluble solvents for the isoflavone values can be used. A preferred solvent for use with aqueous systems due to its ready availability affinity for the isoflavone values and selectivity is ethyl acetate. In an embodiment of the invention, the CSS can be mixed with water to form a dispersion and the dispersion extracted with a solvent for the isoflavone values. Ethyl acetate is particularly effective in that it can extract the isoflavone values with a minimum of saccharides and protein values in the extract. Ethyl acetate is particularly effective when the composition containing the isoflavone values contains substantial amounts of protein and saccharides.

As used herein, the term water immiscible or slightly water soluble refers to compositions which have a solubility in water at 25° C. of less than about 10% by weight.

The term nonsolvent or antisolvent for the isoflavone values as used herein refers to a solvent which is miscible with the extracting solvent but causes the isoflavone values to precipitate from the extract. The nonsolvent is preferably a solvent for fatty materials and is generally of low polarity or is non-polar. Nonsolvents such as low molecular weight $C_4$–$C_{10}$ hydrocarbons have been found to be particularly useful.

If the plant material containing the isoflavone values to be recovered is a solid which can be provided in a finely divided form which does not contain substantial amounts of water, the solid can be directly extracted with the solvent without the addition of water. In this case, the solvent can be water miscible, and preferably is a good solvent for the isoflavone values and a poor solvent for the materials such as carbohydrates, proteins and fats which can be associated with the plant material. However, in the case where fatty material such as fats, fatty acids or esters of fatty acids are present in the plant material to be extracted, fatty materials can be separated from the isoflavone values in a later step in the process. Preferably, the plant materials do not contain substantial amounts of fatty material.

The solvent useful in the practice of the present invention should be readily removable from the isoflavone values without use of high temperatures which temperatures may have an adverse effect on the isoflavone values recovered by the process. The isoflavone values can be recovered in a product containing more than 20% by weight of isoflavone values and preferably greater than 30% by weight and more preferably greater than 40% by weight of isoflavone values. It is possible by proper selection of solvents and process steps, to provide a solid composition containing more than about 50% by weight of isoflavone values and more preferably between about 50 and about 90% by weight of isoflavone values.

As used herein the term isoflavone values means the isoflavone conjugates, isoflavone glycosides, aglucone isoflavones alone or in combination.

The process of the present invention will be illustrated by way of the recovery of isoflavone values from CSS. CSS is a byproduct of the treatment of soybeans and comprises from about 40 to about 50% by weight of moisture and from 50 to 60% by weight of solids. The solids comprise from about 30% to about 45% by weight carbohydrates, from about 5% to about 10% by weight of proteins, from about 7% to about 10% by weight of ash, a small amount of fat and from about 0.3 to about 2.0% by weight of isoflavone values. Purer isoflavone containing products can be more easily obtained from CSS which contains at least 0.5% isoflavone values. Higher concentrations of isoflavone values in the starting material provide for easier recovery of isoflavone values in higher concentrations.

The CSS feed is generally a viscous material which can not be readily contacted with a solvent. In this case, the CSS is first mixed with water in a weight ratio of CSS:water from about 1:0.5 to about 1:10, preferably from about 1:1 to about 1:5 and most preferably from about 1:1 to about 1:3. However, if the viscosity of the CSS is sufficiently low that it can be adequately contacted with the solvent, water need not be added to the CSS before mixing with the solvent. A major portion of the isoflavone values in the CSS comprises genistein which is a Glycoside of genistin. Since the CSS is only partially soluble in water, the water phase is a solution of the soluble material, including a major portion of the isoflavone values present in the CSS, mixed with the insoluble materials. The isoflavone values have an increased solubility in water at a temperature in the range of from about 50° C. to about 90° C. However, since the solubility of the saccharides and proteins is lower at the lower temperatures, it is preferred that the extraction be carried out at a temperature below 50° C. Extraction at the lower temperatures improves the selective recovery of the isoflavone values from the slurry in the extracting solvent. The solvent can be mixed with the slurry of the CSS in water at an elevated temperature and temperature reduced by partial evaporation of the solvent from the mixture under vacuum. The amount of solvent utilized to extract the isoflavone values from the slurry of CSS is used in a weight ratio of solvent to CSS in the range of from about 1:1 to about 30:1 and preferably from about 2:1 to about 20:1, and most preferably from 4:1 to about 12:1.

The extraction can be carried out in multiple extraction stages using fresh solvent in each extraction stage or preferably in a countercurrent manner in which the fresh solvent entering the process contacts the material with the lowest content of isoflavone values.

The aqueous slurry and the solvent are mixed for a time sufficient to extract isoflavone values from the slurry. Contact time is dependent upon the nature of the mixing and contact and is generally in the range from about 30 seconds to about 3 hours and preferably from 1 minute to about 30 minutes and most preferably from about 2 minutes to about 20 minutes.

Since the isoflavone values are more soluble in the aqueous slurry at elevated temperature, it is preferred that the contact between the aqueous slurry and the solvent be carried out at least partially at a temperature below about 50° C. Preferably the lower temperature contact is at the end or near the end of the period of contact between the solvent and the aqueous slurry.

The contact can be done batchwise or in a continuous manner. Preferably, the contacting is done in a countercurrent continuous manner. The countercurrent contacting is preferably carried out in a series of at least two mixing settler zones which can be independently arranged or a series of mixing zones which may also comprise settling zones in a countercurrent extraction column such as a Treybal column, a Scheibel column or a Karr column. Depending upon the amount of solids in the aqueous phase, the agitation of the solvent phase with the aqueous phase should be controlled to prevent the formation of an emulsion.

It has been discovered that the distribution of the individual components comprising the isoflavone values approach more closely the distribution of the isoflavone values in the starting materials if the extraction is done at an acid pH. Preferably the pH is below 6 and more preferably in the range of about 2.5 to 5.5, more preferably in the range of 3 to 5 and most preferably 3.5 to 4.5. However, if a natural distribution of isoflavone value compounds is not required, the extraction can be carried out at a pH as high as about 10.

After the contact between the aqueous slurry and the solvent, the aqueous phase is separated from the solvent phase. The separation can be carried out in a settling zone or a device such as a centrifuge to assure separation between the aqueous phase containing the undissolved solids and the extraction solvent phase.

If a product containing isoflavone values in the range from about 20 to about 35% by weight is required, dependent upon the solvent chosen, the solvent can be merely evaporated from the extracted materials to provide a composition with isoflavone values of at least 20% by weight.

The removal of the solvent must be carried out at a temperature below which the isoflavone values decompose. Preferably, the removal of the solvent is done under a vacuum at a temperature below about 110° C. and preferably below about 100° C., more preferably below about 95° C., and most preferably below about 60° C. The recovered solvent can be recycled and mixed with the CSS and water mixture.

An alternative method for recovering the isoflavone values from the solvent involves crystallization or precipitation of the isoflavone values from the solvent. The solution containing the isoflavone values in the solvent can be cooled to a temperature at which the isoflavone values crystallize or precipitate from the solvent. If the solution of the isoflavone values in the solvent is extremely dilute, the concentration of the isoflavone values in the solvent can be increased by removing a portion of the solvent from the solution. From about 30% to about 99.9% and preferably from about 60% to about 99% of the solvent added can be removed by evaporation to aid in recovery of the isoflavone values by crystallization or precipitation. The solvent can be removed from the solution by heating to an elevated temperature at atmospheric pressure or under a vacuum depending upon the solvent which has been utilized. The increase in concentration of the isoflavone values in the solvent by removal of a portion of the solvent reduces the cooling load and permits recovery of a greater proportion of the isoflavone values at a higher temperature. The product recovered in this manner comprises the highest concentration of isoflavone values but the distribution of the individual components can deviate from the natural distribution.

In an alternative embodiment, the amount of solvent in the solution of the isoflavone values can be reduced by passing the solution at elevated pressure over a Nano membrane having a cutoff point below the molecular weight of the isoflavone values. Nano filtration with a cutoff membrane having a molecular weight cutoff lower than the molecular weight of the isoflavone values, is an energy efficient method for reducing the solvent content and permitting the isoflavone values to crystallize or precipitate from the solution at a higher temperature.

The concentration of isoflavone values of the product recovered by evaporation or crystallization can be further increased in content or purity of the isoflavone values by contacting the composition with a solvent for impurities which are carried by the composition, which solvent is nonsolvent for the isoflavone values or with a solvent for the isoflavone values maintained at a low temperature (cold solvent). Generally, the solvent is a non-polar preferably hydrocarbon material, which can dissolve fatty and oily substances and other hydrocarbon soluble substances from the recovered composition with the increased isoflavone value content and is miscible with the extracting solvent. The recovered material with increased isoflavone value can be contacted with the nonsolvent for the isoflavone values before or after removal of a portion of or substantially all of the solvent for the isoflavone value from the composition. That is, wet or dry crystals or a slurry can be washed with the nonsolvent for the isoflavone values. In a preferred embodiment, the major portion of the solvent is removed (at least about 90% by weight of the solvent) to form a slurry of the isoflavone values in the solvent, an antisolvent or nonsolvent for the isoflavone values optionally containing water is added to the slurry to precipitate additional isoflavone values and dissolve fatty materials in the slurry and the precipitated and crystallized isoflavone values are separated from the mixture of solvent and antisolvent or nonsolvent for the isoflavone values. This method can produce a product containing more than 50% by weight isoflavone values and preferably a product containing more than 60% and more preferably a product containing at least 70% isoflavone values.

In an embodiment of the invention, after the aqueous material has been separated from the solvent containing the isoflavone values and a portion of the solvent removed, the solution or slurry of the isoflavone values in the solvent can be diluted with a nonsolvent or antisolvent for the isoflavone values. Such solvents are generally non-polar materials such as hydrocarbons and are solvents for fatty materials. The preferred hydrocarbons are low boiling materials such as butane, pentane, hexane, heptane, and octane. Lower or higher boiling point materials can be utilized but they present special problems in the relation to the low boiling points of the low molecular weight hydrocarbons and the higher boiling points of the higher molecular weight materials. Normally, the isoflavone values can be precipitated from the solution in the solvent by addition of only small amounts of a non-polar nonsolvent for the isoflavones. Generally, an amount of nonsolvent of from about 2% by weight to about 1,000% by weight of the solution or slurry of the isoflavone values in the solvent can be used to precipitate the isoflavone values from the solvent. However, higher amounts of the nonsolvent can be utilized but does not result in a substantially greater recovery of the isoflavone values and requires a substantial amount of equipment to separate the nonsolvent for the isoflavones from the solvent for the isoflavones.

The precipitation is generally carried out at a temperature from about 0° C. to about 50° C. Preferably, the precipitation is carried out at low temperatures, in the range of from about 10° C. to about 35° C. Since the isoflavone values have increased solubility in the solvent for the isoflavone values at temperatures above about 50° C., it is preferred that the nonsolvent for the isoflavone values be added to the solution of the isoflavone values in the solvent and the mixture cooled to a temperature less than about 50° C. and preferably below about 30° C.

The mixture of the nonsolvent for the isoflavone values with the solution in the extracting solvent or the slurry can provide isoflavone particles of a small size, which are difficult to separate from the solvents. Applicants have unexpectedly discovered that addition of small amounts of water to the mixture causes the small particles to agglomerate so that they can easily be recovered from the slurry. Generally addition of water of from about 0.5% by weight to about 20% by weight of the nonsolvent or antisolvent is sufficient to agglomerate the particles. A preferred amount of water is from about 1.5% to about 10% by weight of the nonsolvent and most preferably about 2% to about 5% by weight of the nonsolvent.

In an alternate embodiment, the nonsolvent for the isoflavone values can be a supercritical material such as supercritical carbon dioxide or subcritical liquid carbon dioxide. In this embodiment, the supercritical or liquid carbon dioxide is mixed with the solution of the isoflavone values in the solvent to precipitate the isoflavone values from the solvent. The precipitated solids are separated from the solvent supercritical or liquid carbon dioxide mixture, washed with supercritical carbon dioxide and dried. The mixture of the solvent for the isoflavone values and the carbon dioxide is then passed through a pressure reducing zone to a separator where the carbon dioxide is separated from the solvent. The carbon dioxide is then compressed, cooled and returned to the process as the supercritical fluid. The solvent is then returned to the step of mixing with the aqueous slurry of the CSS. The pressures and temperatures for use of the supercritical carbon dioxide is well known to one skilled in the art. Instead of carbon dioxide, it is also possible to utilize other supercritical gasses, however, the supercritical range for carbon dioxide is practical for commercial operations.

The supercritical fluid is utilized at from about 10% to about 1000% by weight of the solution of the isoflavone values in the solvent. The supercritical fluid is mixed with the solution of the isoflavone values. The isoflavone values precipitate from the solution. The precipitated isoflavone values are then separated from the liquid and can be washed with the nonsolvent for the isoflavone values to remove the solvent and any impurities which are present in the precipitated material which are soluble in the nonsolvent for the isoflavones. The nonsolvent for the wash can be the supercritical fluid.

The use of supercritical fluid presents an advantage in the process in that the supercritical fluid can be recovered from the solution by reducing the pressure, removing the gaseous phase and compressing the gaseous phase to the supercritical state.

The process will be explained in relation to the following process schematic diagrams.

FIG. 1 is a diagrammatic representation of the extraction zone in the process of the present invention.

FIG. 1 is a schematic representation of a mixing and settling zone utilized in the practice of the present invention. Extraction and settling zone 1 comprise a mixing zone 2 and a separation zone 9. The plant material to be contacted with the solvent is introduced into the mixing zone through conduit 3. The solvent is introduced into the mixing zone through conduit 4 and water can be introduced into the mixing zone through line 5. If the plant material is difficult to pump, the plant material (particularly CSS) is first mixed with water before entering the mixing-extraction zone, and the mixture would enter through the same conduit (3). As discussed above, water is an optional material that is utilized when the plant material is difficult to contact with the solvent. The water can reduce the viscosity or dissolve the plant material or at least partially dissolve the plant material. The mixing and extraction is preferably carried out at a temperature below about 100° C. and preferably below about 80° C. and most preferably below about 50° C. The mixture of the solvent solution of the extracted isoflavone values, a water solution of some of the impurities and solids passes through conduit 6 to separation zone 9. In separation zone 9 the solvent phase is separated from the undissolved plant material and the water solution. Separation zone 9 can be a quiescent zone or can be a liquid cyclone centrifuge or the like. The solvent containing the dissolved isoflavone values passes through conduit 7 for further processing or to a further mixing settling zone. The plant residues and water if present passes out of separation zone 9 through line 8, and can be further treated to remove solvent and water present in the mixture or passed to a further mixing settling zone. The plant material, when recovered from the aqueous phase, has approximately the same composition as the feed except for the isoflavone values. The recovered plant material has nutrient value and can be mixed with other constituents to form an animal feed. The solvent can be recovered and returned to the mixing zone. The solution of the isoflavone values in the solvent in conduit 7 can be passed through a filter means to remove solid particles and/or a coalescing means which can separate fine droplets of an aqueous phase if present from the solvent solution. Filter or droplet separation means decreases the amount of impurities which may pass out of the system with the solution of the isoflavone values in the solvent. If the solvent and aqueous phase are not passed to further mixing-settling zones, the solvent and water can be separated from the two phases to recover the isoflavone values and the nutrient values in the aqueous phase.

Figure 2:
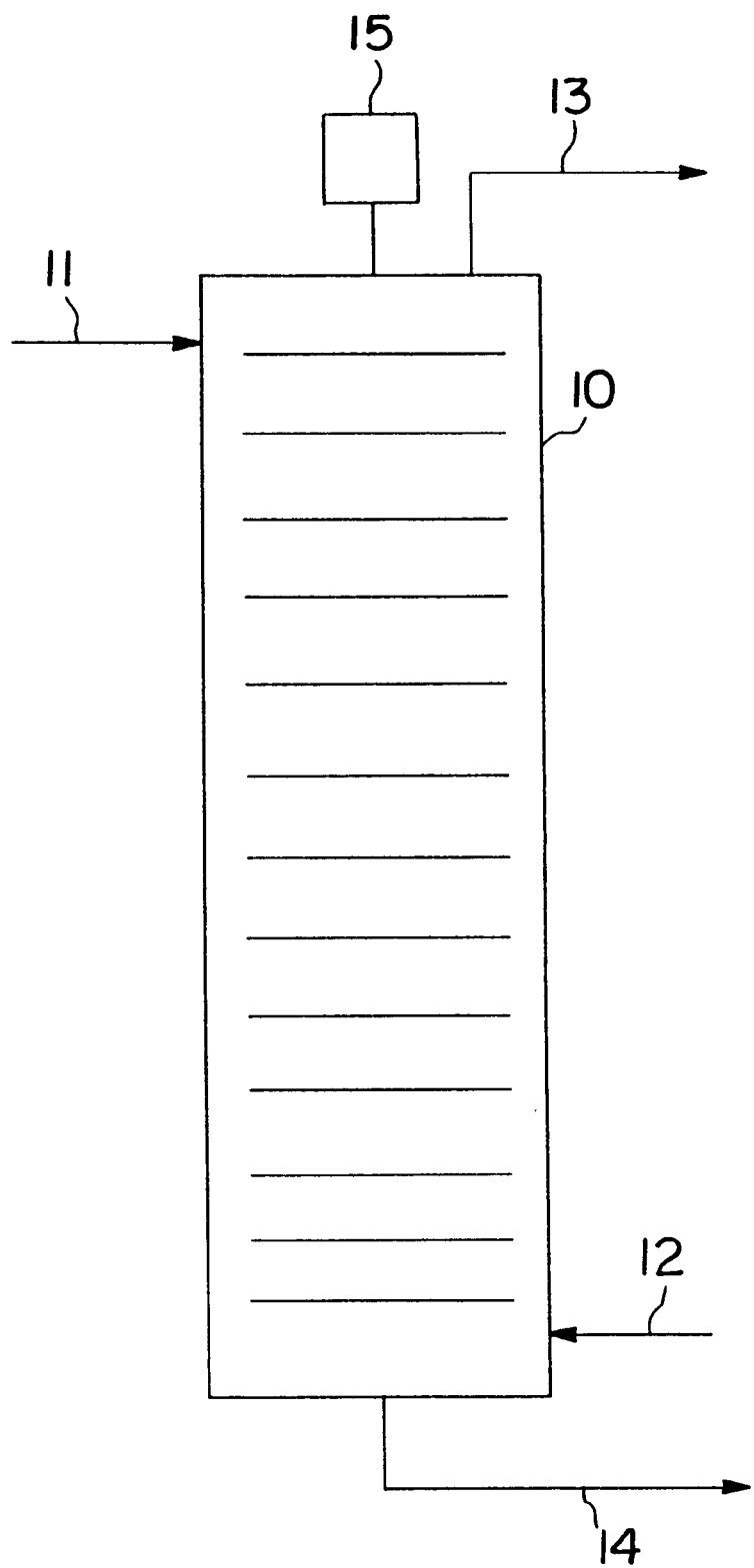
FIG. 2 is a diagrammatic representation of a continuous countercurrent mixing extraction zone.

FIG. 2 is a schematic representation of a continuous countercurrent contacting zone for extracting the isoflavone values from a mixture of water and the plant material. In extraction zone 10, a heavier phase is introduced into the extraction zone through conduit 11 near the top of the column. The lighter phase is introduced near the bottom of the column through line 12. Generally, the solvent is the lighter phase. The solution of the isoflavone values in the solvent is removed from the countercurrent extraction zone through conduit 13. The heavier phase which is usually the water phase, containing the residues of the plant material, is removed from the continuous countercurrent contacting zone through line 14. The moving means 15 provides agitation and mixing to the contents of the column.

The countercurrent contacting zones generally comprise a number of contacting zones supplied with means for agitation in the contacting zone by the moving means 15. Countercurrent extraction columns are well known in the art and are exemplified by columns such as a Treybal column, a Scheibel column or a Karr column. In addition, columns which do not provide internal agitation such as perforated tray columns and the like can also be utilized if the solids content of the aqueous phase is sufficiently low that the columns do not plug. A column type apparatus is shown but a series of mixing settling zones can be used.

The countercurrent extraction zone can be operated at ambient temperature or at elevated temperatures below about 100° C. Preferably, if the isoflavone values are more soluble in the water phase at an elevated temperature, it is preferred that the lower portion of the column be operated at a higher temperature (about above 50° C.) than the upper portion of the column.

The plant residues and the aqueous phase which are removed through conduit 14 can be treated to remove any solvent which may be dissolved or entrained in the aqueous phase, the solvent recovered, the water removed and the plant matter mixed with other components to provide an animal feed supplement. The extract is removed from the column through line 13 and can be filtered or passed through a coalescing means to ensure that solids and any droplets of the aqueous phase containing impurities are not transferred to the isoflavone value recovery portion of the process. In one embodiment of the invention, the isoflavone values are recovered from the solution of the isoflavone values merely by removing the solvent from the dissolved material. The product containing the isoflavone values obtained by removing the solvent from the dissolved material is generally greater than a 20% isoflavone values by weight of the product. The concentration of isoflavone values in the product can be further increased by washing with a composition which is a nonsolvent or antisolvent for the isoflavone values, but is a solvent for some of the impurities such as fats and lipids which are present in the product. Hydrocarbon solvents such as propane, butane, pentane, hexane, heptane, octane and the like can be utilized. Preferably the hydrocarbon solvents are hexane, heptane, octane or mixtures thereof since they are readily available and have boiling points in a range which make them easy to remove from the product and in addition can be utilized without the need for high pressure equipment.

Figure 3:
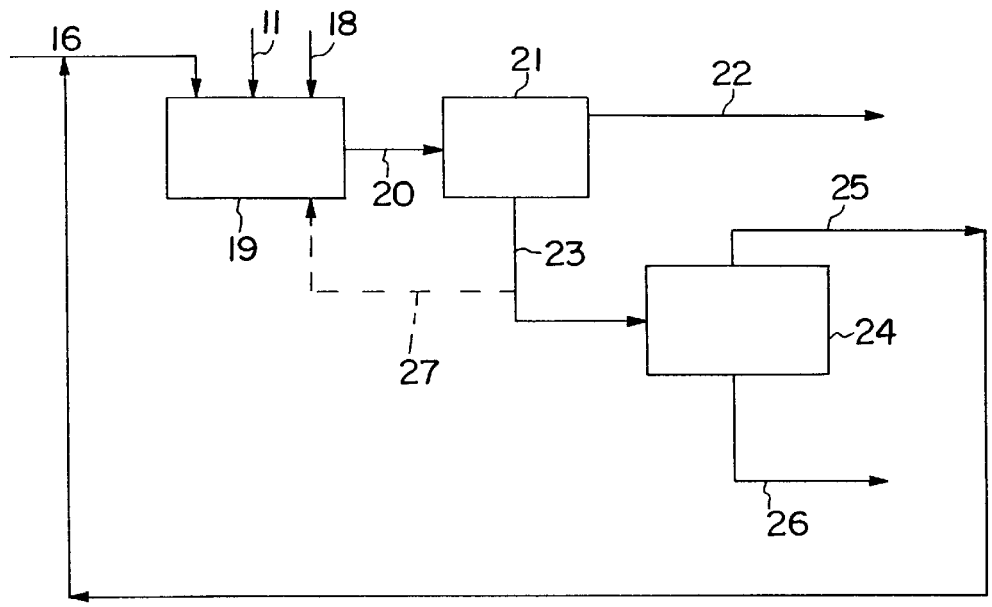
FIG. 3. is a diagrammatic representation of a mixing-extraction-separation zone with a zone for treatment of the aqueous phase separated from the solvent phase.

FIG. 3 is a schematic representation of the mixing-extraction-separation zone and a zone for treatment of the aqueous phase of the process of the present invention. Solvent is introduced into the mixing and extraction zone 19 through conduit 16. The plant material containing the isoflavones is introduced through line 17 and generally water is introduced in line 18 or can be introduced mixed with the plant material. If the plant material is CSS which has a high viscosity, water is mixed with the CSS to reduce the viscosity before entry into mixing and extraction zone 19 to permit adequate contact between the solvent and the plant material from which the isoflavone values are to be recovered. A preferred solvent for use in the method where substantial amounts of water is present is ethyl acetate. The solvent, plant material and optionally water are intimately mixed in mixing and extraction zone 19 for a sufficient length of time to permit the solvent to extract a portion of the isoflavone values from the plant material. The mixture passes through conduit 20 to separation zone 21. Separation zone 21 can be a settling zone, a centrifuge, a liquid cyclone and the like which are known to be useful for separating liquids with different densities, which may contain solids, from each other. The solvent containing the isoflavone values passes out of separation zone 21 through conduit 22 to an isoflavone recovery zone. The water phase containing solid materials, which have not been dissolved, pass through conduit 23 to a solvent recovery-solid treatment zone 24. In treatment zone at 24, the aqueous phase is treated to recover solvent which may have been dissolved in the aqueous phase or is present in small droplets which do not separate in the separation zone 21. The recovered solvent is passed through conduit 25 to the mixing-extraction zone. The aqueous phase containing solid material which has not been extracted, whether in solid form or dissolved in the aqueous phase leaves the process through conduit 26 and can be further treated to remove all or a portion of the water contained therein and the plant material which has substantially the same composition as the feed with a lower isoflavone value content can be utilized as a portion of an animal feed or the like.

FIG. 3 shows one mixing extraction and separation zone. However, the mixing and extraction is preferably done in a plurality of countercurrent stages. That is, the aqueous phase containing soluble and insoluble plant material is contacted at least two times with the solvent for the isoflavone values and preferably in a countercurrent manner. The aqueous phase can be recycled from the separation zone 21 through line 27 to return to the mixer to be contacted with additional fresh solvent. In an alternate embodiment, the mixing and separation zone can comprise multiple mixers and separation zones and the aqueous phase containing undissolved solids can be contacted in a countercurrent manner with a solvent. In this case, the fresh solvent would contact the aqueous phase containing the lowest concentration of isoflavone values and after contact with the fresh solvent, the aqueous phase would then pass to the treatment zone 24. The aqueous phase containing the plant material feed would first contact the solvent containing the highest concentration of isoflavone values. After contact with the solvent containing the highest concentration of isoflavone values, the aqueous phase would be separated from the solvent phase and the aqueous phase then passed to a second mixing extraction settling zone to be contacted with solvent containing a lower concentration of isoflavone values. The solvent containing the highest concentration of isoflavone values from the first contact settling zone would then pass to the zone for recovery of the isoflavone values from the solvent. This process scheme is equivalent to the countercurrent contacting which occurs in the countercurrent contacting zone 10 in FIG. 2. A similar process is carried out in the continuous countercurrent column contacting zone except in some cases there is no settling zone between contact stages. The settling zones may only be provided at the top and bottom portions of the column continuous contacting zone.

Figure 4:
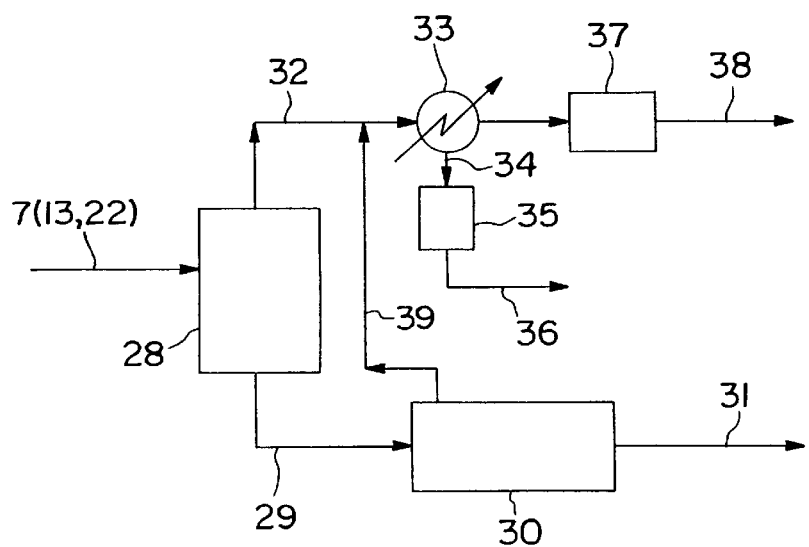
FIG. 4 is a diagrammatic representation of a process for recovering a solid product containing a higher concentration of isoflavone values by means of evaporating the solvent.

FIG. 4 is a schematic representation of the process of the present invention wherein the isoflavone values are recovered from solution in a solvent by evaporation of the solvent.

The solution of the isoflavone values in the solvent is introduced into evaporation zone 28 through the conduits 7 (13,22) from the extraction and separation zone. The solvent is removed under mild conditions which can include a vacuum where the solvent vapors pass out of evaporator zone 28 through line 32 and are condensed in condenser 33. The condensed solvent passes through line 34 to receiver vessel 35 and then is transferred to a storage tank or to the mixing settling zone through conduit 36. A slurry of the precipitated isoflavone product and solvent passes through conduit 29 to solvent removal zone 30. In solvent removal zone 30, the remaining solvent is separated from the isoflavone value containing product. Solvent removal zone 30 is generally a heated agitated zone which may be operated under reduced pressure to reduce the amount of solvent in the isoflavone value containing product to as low a level as commercially feasible. Preferably, the solvent is reduced to a range of preferably less than about 5 parts per million, and more preferably less than about 1 part per million. As shown in FIG. 4, the solvent removal zone 30 is operated under a reduced pressure, the solvent vapors are passed to a condenser in the vapor line from the evaporator 28. The dried, solvent free, isoflavone value containing product is removed from the solvent removal zone 30 through conduit 31. Solvent removal zone 30 can be a heated multiple screw type dryer, a heated paddle mixing type apparatus, a fluidized bed, a tray dryer, microwave dryer or other means known for applying heat to remove solvent or water from a solid material. In an alternative embodiment, the mixture of the precipitated isoflavone values can contain a sufficient amount of solvent to be in the form of a slurry which can be separated by liquid-solid separating means such as filter or centrifuge before passing to the heated solvent removal zone.

The product obtained by removal of the solvent from the dissolved isoflavone value containing solution provides a product containing at least about 20% by weight of isoflavone values. In an alternative embodiment, prior to passing to the solvent removal zone 30, the solids can be washed with a nonsolvent for the isoflavone values or with fresh solvent, which can be a solvent for the isoflavone values. Optionally a small amount of water can be mixed with the nonsolvent for the isoflavone values to make recovery of the isoflavone values more easily accomplished. This preliminary wash before solvent removal or drying removes solvent liquid which can contain impurities which would appear in the isoflavone value containing product after complete removal of the solvent. The removal of the liquid which is carried with the precipitate from the evaporator and dissolution of some of the impurities decreases the impurities in the isoflavone value containing product. Vacuum producing zone 37 applies a vacuum to at least the solvent removal zone 30 and uncondensed vapors are removed through conduit 38. FIG. 4 shows evaporation zone 28 as operated under a vacuum. Vacuum is not required in solvent evaporation zone 28 if the solvent has a sufficiently low boiling point.

Products with a concentration of isoflavone values above about 30% by weight can be obtained by washing the isoflavone containing product with a nonsolvent for the isoflavone values.

Figure 5:
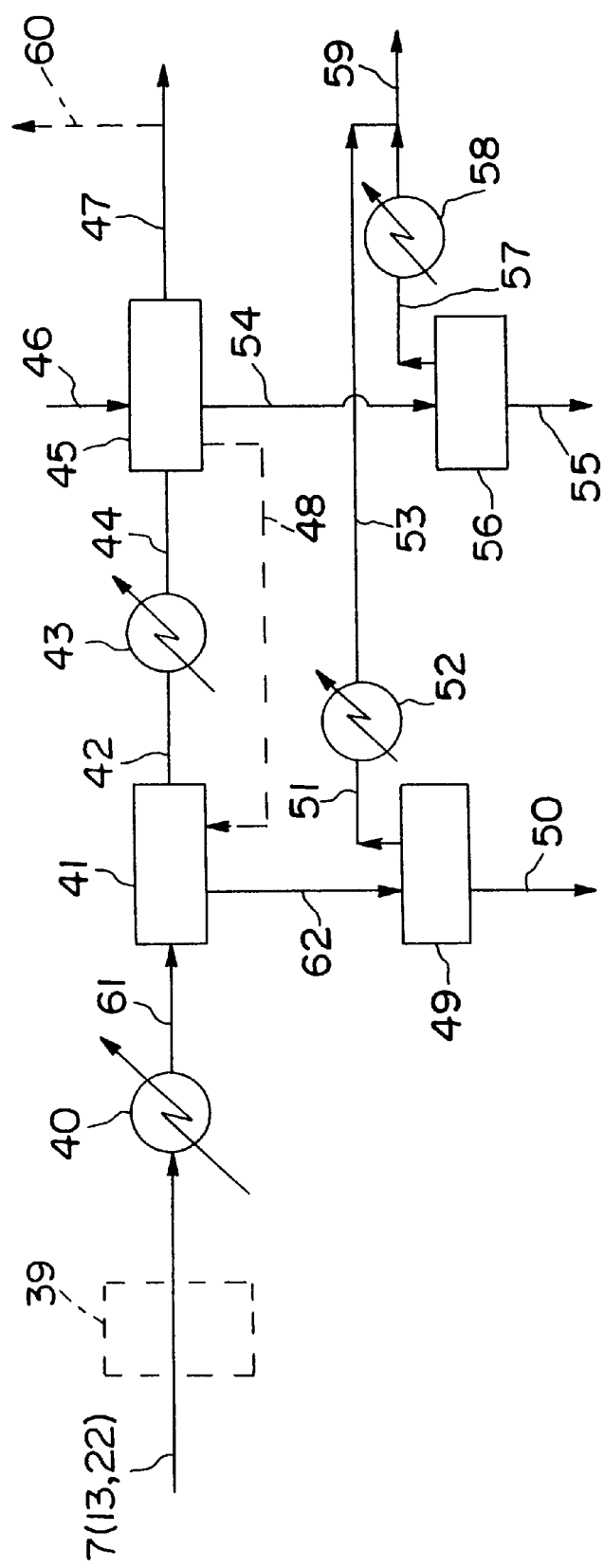
FIG. 5 is a diagrammatic representation of a process for recovering the isoflavone values by a crystallization method.

FIG. 5 is a schematic representation of the process of the present invention wherein the product containing the isoflavone values is recovered from the solvent by crystallization. The embodiment shown in FIG. 5 illustrates obtaining two products with different concentrations of isoflavone values from the solution of isoflavone values in a solvent. The solution of isoflavone values in the solvent from the extraction and separation zone is introduced into the process of the present invention through line 7 (13,22). Preferably the solution of the isoflavone values in the solvent passes through an evaporation zone shown as a dotted line 39 to remove a portion of the solvent and increase the concentration of the isoflavone values in the solvent. From about 30% by weight to about 99% by weight of the solvent can be removed in the evaporation zone 39. The solution or slurry of the isoflavone values in the solvent then passes to a cooler/crystallization zone 40 where the solution is cooled and crystals of the isoflavone value containing product are formed. A slurry of the solid product passes through conduit 61 to separation zone 41 which can be a filter, centrifuge or like means for separating a solid from a liquid. The solid separated from the solution can be washed to remove mother liquor and then pass through conduit 62 to the solvent removal zone 49. In solvent removal zone 49, the residual solvent is removed from the crystals. The solvent free product containing the isoflavone values is removed from the solvent removal zone 49 through conduit 50. The evaporated solvent passes through conduit 51 through condenser 52 and the liquid passes through conduit 53 to conduit 59 which passes the solvent to storage or the extraction separation zone.

The liquid phase from the solid separation zone 41 is further cooled in crystallization zone 43 and a slurry of the solids in the solvent pass through conduit 44 to solid separation zone 45. Crystallization zone 43 can also be a partial evaporation zone where an additional portion of the solvent is removed along with the additional cooling. In solid liquid separation zone 45, the solid materials which have precipitated from the liquid solution are separated from the liquid and can be optionally washed by fresh solvent or a nonsolvent for the isoflavone values, optionally containing from about 0.5% by weight to about 20% by weight of water, which is introduced through conduit 46. The solvent or nonsolvent which was utilized to wash the precipitate or crystals in the liquid solid separation zone 45 can pass out of the solid liquid separation zone with the solid or can be recycled through line 48 to wash the crystals in the first solvent liquid separation zone 41. The solvent from which the isoflavone values have been crystallized pass out of the solid liquid separation zone through line 47 and can be returned to the mixing settling zone. At times depending upon the source of the plant material, impurities can build up in the solvent. If the impurity level becomes high, a side stream of the solvent can be removed through conduit 60, the solvent separated from the impurities and the solvent returned to the extraction separation zone.

If the crystals are washed by a nonsolvent or antisolvent for the isoflavone values, a mixed solvent stream is formed and the different solvents separated before being returned to the process.

The solid material from the liquid solid separation zone 45 passes through line 54 to solvent removal zone 56. The solvent free isoflavone containing product passes through line 55 to the storage and shipping area. The solvent removed from the solid passes through conduit 57 to condenser 58 and through conduit 59 returns to the mixing, extraction separation zone. The solvent removal apparatus removes the solvent by a gentle heating process which can be carried out at a reduced pressure if required.

Generally, the temperature is maintained below about 100° C. and is operated at as low a temperature as possible to prevent degradation of the isoflavone value containing product. By the crystallization method, it is possible to provide products containing greater than about 50% by weight of isoflavones and preferably greater than about 60% by weight of isoflavone values. Product from solvent removal zone 49 generally is of a higher purity than the product obtained from the solvent removal zone 56. The two products can be mixed or sold as different grades of product.

FIG. 5 discloses a dual crystallization and a separation process. However, if only a single product is required, a single crystallization zone can be utilized.

Figure 6:
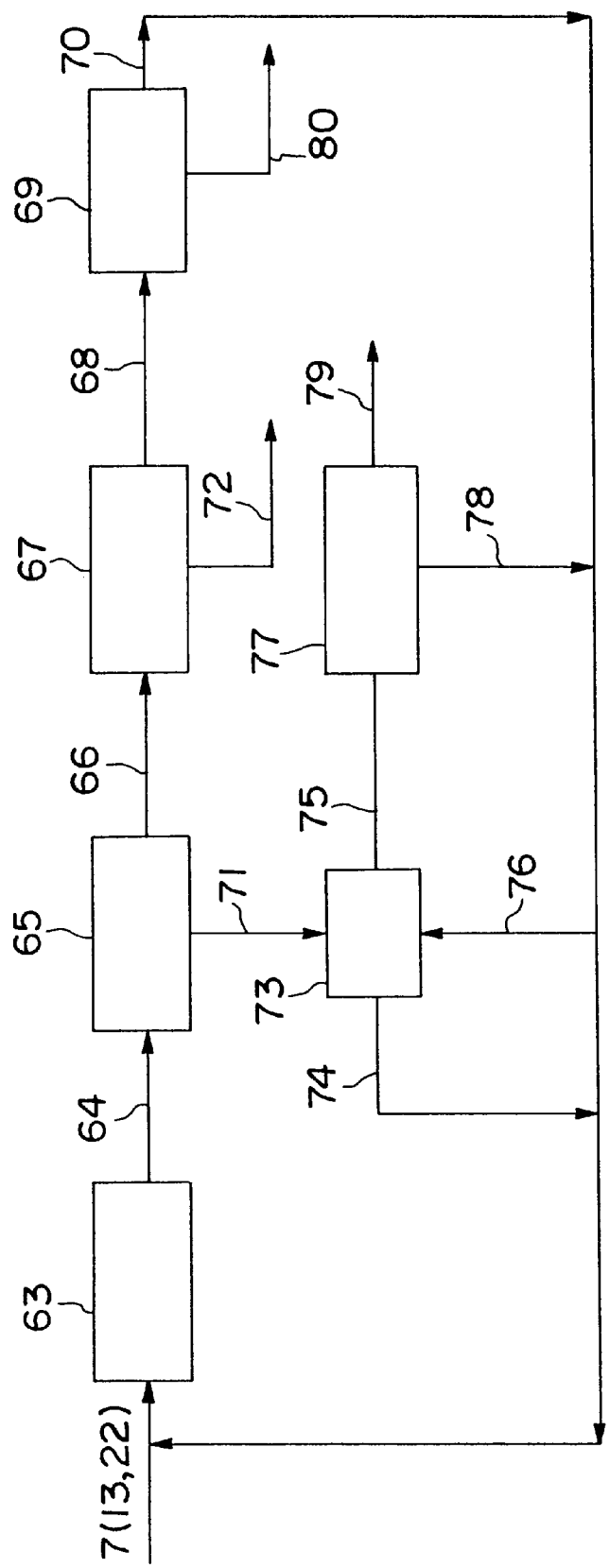
FIG. 6 is a diagrammatic representation of a method for recovering the isoflavone values from the solvent by precipitation upon addition of a nonsolvent for the isoflavone values to the solution of the isoflavone values.

FIG. 6 is a diagrammatic representation of the process of the invention wherein the isoflavone value containing product is precipitated from the solvent solution by the addition of a composition which is a nonsolvent or antisolvent for the isoflavone values but is soluble in the solvent. The addition of the composition which is a nonsolvent for the isoflavone values causes the isoflavone values to precipitate from the solution. The solids can then be separated from the solvent by known liquid separation means. The precipitation is generally carried out at ambient temperatures by the addition of from about 2% by weight to about 2000% by weight and preferably from about 50% by weight to about 500% by weight based on the weight of the solution of the isoflavones. Larger amounts of nonsolvent for the isoflavone values can be incorporated into the mixture but only a marginal increase in precipitation of the isoflavone values is experienced.

The solution of the isoflavone values in the solvent is the mixture from the extraction separation zone or can be a mixture in which a portion of the solvent has been removed which enters through conduit 7 (13,22) to mixing zone 63. The nonsolvent or antisolvent for the isoflavones is introduced into the system through conduit 70 and can be mixed with the solution of the isoflavone values in the solvent in the line 7 (13,22) just before it enters the mixing zone or it can be introduced separately into the mixing zone 63. In mixing zone 63, the nonsolvent or antisolvent for the isoflavone values, the solution of the isoflavone values in the solvent for the isoflavone values and, optionally from about 0.5% by weight to about 20% by weight of water, based on the weight of the nonsolvent, are mixed and isoflavone values and other materials which are present in the solution are precipitated as a solid material. The slurry of the solids in the mixed solvent solution pass through conduit 64 to liquid solid separation zone 65. In liquid solid separation zone 65 the liquid material is separated from the precipitated solids and the liquid passes through conduit 66 to solvent recovery zone 67. In solvent recovery zone 67, the mixture of solvents is separated from any solid materials which remain in the mixed solvent. These solids are passed out of solvent recovery zone 67 through conduit 72 and can be further treated to recover isoflavone values present therein or the material can be recycled to the mixing-extraction-separation zone. The mixed solvents pass through conduit 68 to solvent separation zone 69 where the solvent for the isoflavone values is separated from the nonsolvent for the isoflavone values. The nonsolvent for the isoflavone values is then recycled through line 70 to the mixing precipitation zone 63. The solvent for the isoflavone values is returned to the mixer extraction settling zone through conduit 80.

The liquid solid separation zone 65 can comprise an apparatus such as a centrifuge, a filter or other means known for separating solids from liquids. The solids separated from the solvents passes through conduit 71 to solid wash zone 73 where the recovered solids are washed with a nonsolvent or antisolvent for the isoflavone values, optionally containing a small amount of water, or the extracting solvent which are introduced through conduit 76. The mixture of solvents which has contacted the precipitated solids from the liquid solids separation zone 65 passes out of solids washing zone 73 through conduit 74 and can be returned to the mixing precipitation zone 63 for mixing with the solution of the isoflavone values in the solvent. The washed precipitate passes through conduit 75 to solvent removal zone 77 wherein the solvents are removed from the precipitated materials and recycled to the mixing zone through conduit 78 and conduit 70. The substantially solvent free isoflavone values pass from the system through conduit 79. The treated material which is removed from the evaporator 67 through conduit 72 contains isoflavone values and can be sold as a separate product or recycled to the mixer extraction separation zone. The isoflavone value recovery process set forth in FIG. 6 is useful in that the isoflavone values can be recovered at a high purity wherein a major portion of the impurities remain in the solvent system.

The nonsolvents or antisolvents for the isoflavone values are generally non-polar materials such as butane, pentane, hexane, heptane, octane, and the like. Generally the nonsolvent for the isoflavones is selected so that the nonsolvent can be readily separated from the solvent for the isoflavone values without difficulty without the requirement for a multiple fractional distillation apparatus.

Although the lower molecular weight alkanes are particularly useful, other hydrocarbons or other materials which are nonsolvents for the isoflavone values and are soluble in the solvent for the isoflavone values can be utilized. However, due to their suitable boiling point ranges and ready availability, the lower alkanes have been found to be particularly useful.

Figure 7:
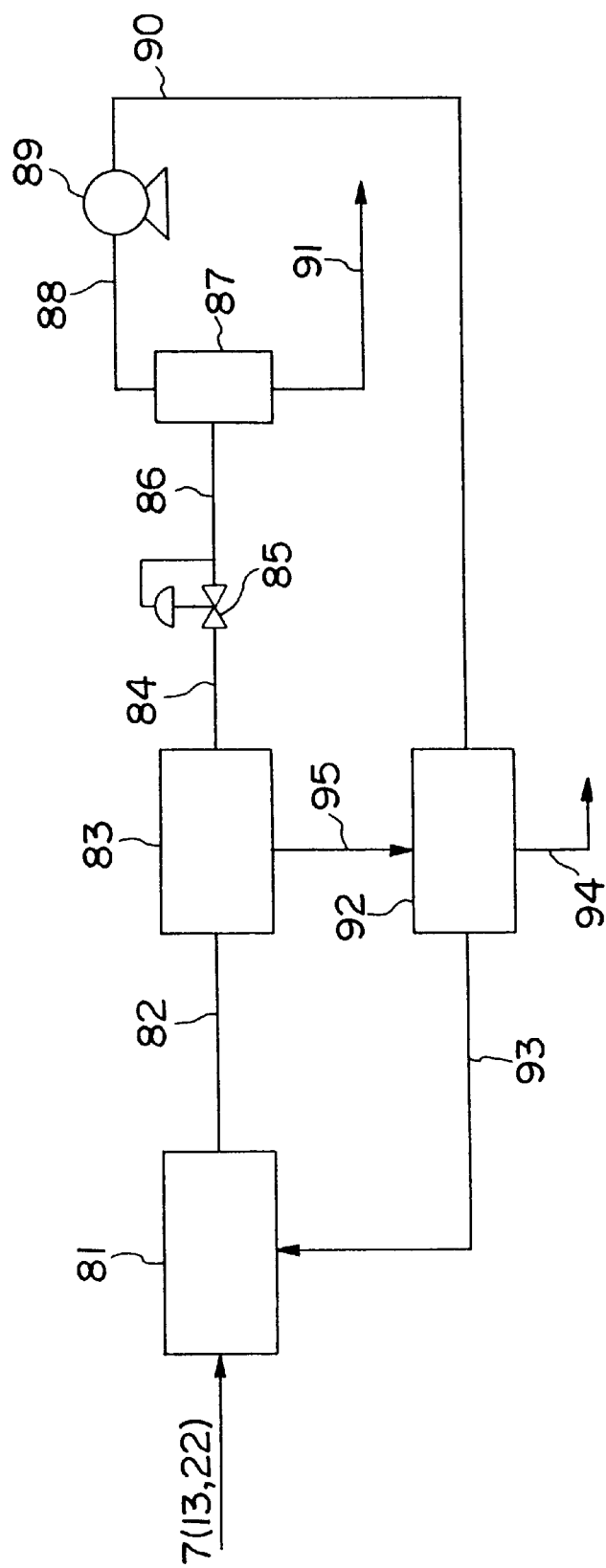
FIG. 7 is a diagrammatic representation of a process for precipitating the isoflavone values from the solvent by the addition of a supercritical gas such as $CO_2$ to a solution of the isoflavone values.

FIG. 7 is an embodiment of the process set forth in FIG. 6 wherein a nonsolvent for the isoflavone values is a supercritical fluid such as carbon dioxide. Since the process is operated at supercritical conditions of carbon dioxide, a mixing and liquid solid separation zone must be operated at an elevated pressure to maintain the carbon dioxide at supercritical conditions. The solution of isoflavone values in the solvent is introduced into mixing zone 81 through conduit 7 (13,22) and is mixed with supercritical carbon dioxide which enters the mixing zone through conduit 93. In the mixing zone, the isoflavone values are precipitated from the solvent and the slurry passes out of the mixing zone through conduit 82 to liquid solid separation zone 83. In liquid solid separation zone 83, the isoflavone value containing product is separated from the mixed solvent system and passed through conduit 95 to solid washing drying zone 92. In solid washing drying zone 92, precipitated solids are washed with supercritical carbon dioxide and the supercritical carbon dioxide separated from the solids and the solids products containing the isoflavone values passed out of washing drying zone 92 through conduit 94. The mixed solvents pass from the liquid solid separation zone 83 through line 84 and a pressure reducing means 85. The mixed solvents at a reduced pressure pass through conduit 86 to gas liquid separation zone 87. In the gas liquid separation zone 87 which is at a pressure lower than the critical pressure for $CO_2$, the solvent for the isoflavone values which is a liquid is separated from the gas which is no longer at supercritical conditions. The gas phase passes from the gas liquid separation zone 87 through conduit 88 to compressor 89 and is recycled through line 90 to the washing drying zone 92 and then to the mixer 81. The liquid solvent for the isoflavone values passes out of liquid gas separation zone 87 through conduit 91. The solvent contains minor amounts of isoflavone values and any other dissolved materials which were not precipitated by the non-solvent for the isoflavone. values. The solvent in conduit 91 can be passed directly to the mixing, extraction separation zone or the solvent can be separated from the dissolved solids. If the dissolved solids tend to build up in the solution, it may be necessary to remove a small side stream of the solvent and separate the solvent from the dissolved solids.

Figure 8:
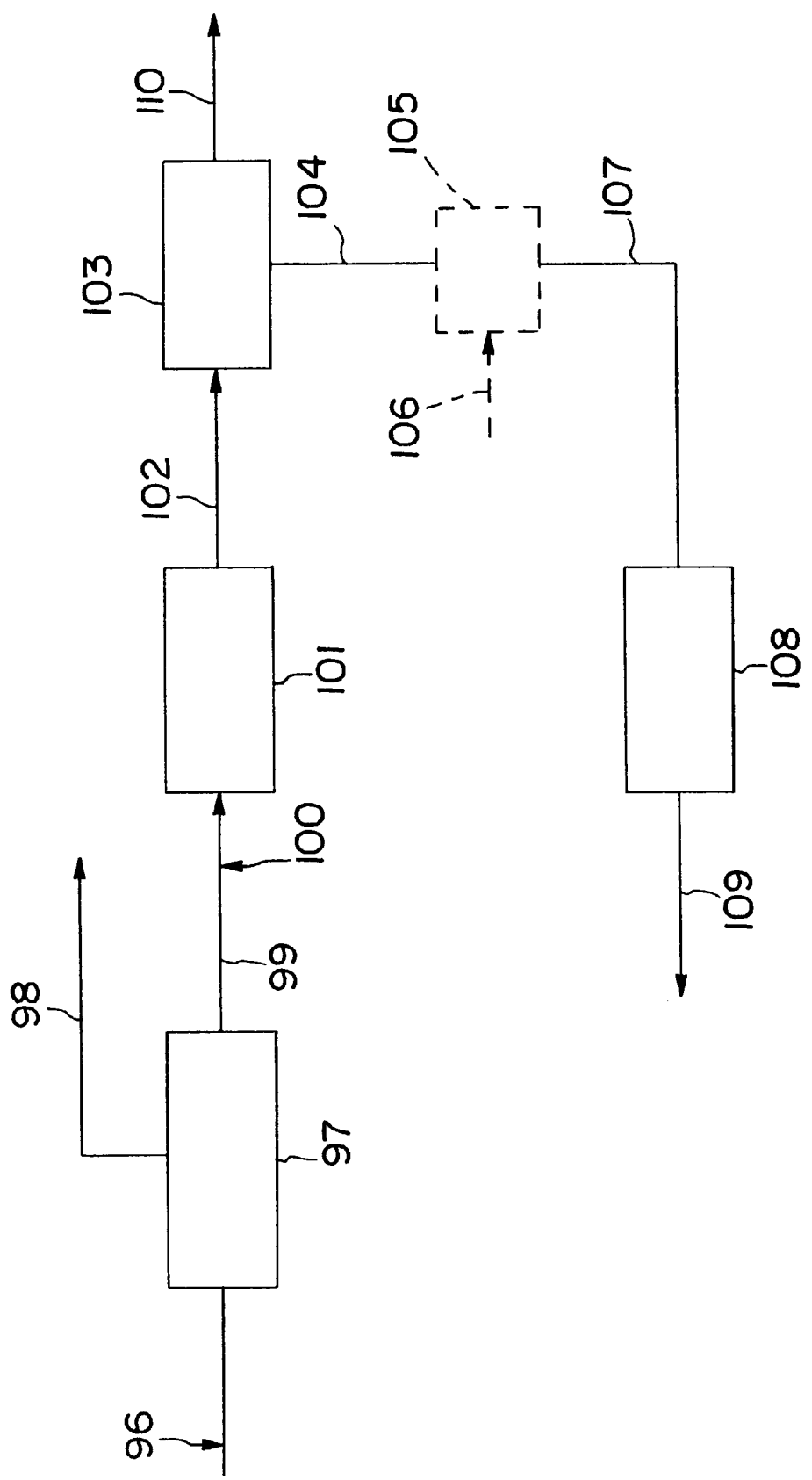
FIG. 8 is a diagrammatic representation of a process in which the solvent is evaporated to form a slurry of the isoflavones in the solvent and a nonsolvent or antisolvent for the isoflavones values is added to the slurry.

FIG. 8 is a diagrammatic representation of a process for recovering the isoflavone values from the extract. The extract enters evaporation zone 97 through line 96. The extract is heated in evaporation zone 97 and the solvent vapors are removed from the evaporation zone through line 98. The evaporation is continued until a flowable slurry of the isoflavone values in the solvent is obtained. The slurry of the isoflavone values in the solvent is passed to mixing zone 101 through line 99. A nonsolvent for the isoflavone values or an antisolvent for the isoflavone values containing from about 0.5% to about 20% by weight of water is mixed with the slurry in line 99 and enters the mixing zone 101 with the slurry. The slurry is mixed with the water containing nonsolvent for the isoflavone values and passes to liquid solid separation zone 103 through conduit 102. In separation zone 103, the solid particles are separated from the solvent which leaves the separation zone through line 110. The solids contaminated with a small amount of the mixed solvent pass through line 104 and optionally can be washed with fresh solvent or the nonsolvent in wash zone 105. The solvent enters through line 106. The mixture of the crystals and the solvent material passes to separation drying zone 108 wherein the wash solvent if utilized is separated from the crystals and the crystals dried. The product leaves drying zone 108 through conduit 109. By this process, a composition containing more than about 40% and preferably more than about 50% isoflavone values can be produced. The amount of lipids or fat like materials in the product are removed by the final wash and optional additional wash to provide a high purity isoflavone product.

In the purification step, the solvent is removed form the extract until a flowable slurry is produced. Generally, this required removal of at least about 90% of the solvent in the mixture. Preferably, at least about 95% and at times 99% of the solvent can be removed, providing a flowable slurry of the isoflavone values in the extracting solvent. The addition of the water containing nonsolvent for the isoflavone values precipitates additional isoflavone values from the remaining solvent and in addition washes the precipitate and removes any fatlike material which may be present. The removal of the fatlike materials substantially increases the concentration of the isoflavone values in the dried product. The addition of water to the nonsolvent increases the yield of isoflavone values, reduces the amount of isoflavone values which remain in the solvent thereby increasing the purity of the recovered product. The water may dissolve water soluble impurities in the solid material.

Solvents useful in the present invention cover a broad range of materials in which the isoflavone values are soluble. The choice of a solvent depends upon whether the isoflavone values are extracted from a mixture of the plant material and substantial amounts of water or extracted directly from a dry material such as defatted soybean meal or flour. Solvents such as alcohols, ketones, lower fatty acid alkyl esters, or any of the chlorinated hydrocarbons such as chloroform, methylene, chloride, methyl chloride and the like and other materials which are solvents for the isoflavone values. If water is present, the solvent should be immiscible or only slightly soluble in the water phase. This provides for ready separation of the solution of the isoflavone values from the aqueous phase. Preferably the solvent is a selective solvent for the isoflavone values.

The extraction is generally carried out at a temperature below about 100° C. Preferably, a portion of the extraction is carried out at a temperature below about 50° C. At a temperature of about 50° C. and above, the solubility of the isoflavone values in the water phase tends to increase, and large amounts of impurities tend to enter the selective solvent.

As used herein, the term isoflavone values refers to the isoflavones such as the aglucones and isoflavone derivatives such as the glycosides and malonyl esters which are present in the plant material.

Applicants have set forth several embodiments of the process of the invention. Applicants do not intend to be limited by the embodiments set forth but to include other embodiments which would be known to or obvious to one skilled in the art from the embodiments set forth herein.

The nature and construction of the mixing extraction zones, the liquid solid separation zones and the mixing zone would be well known to one skilled in the art and should be constructed of materials which do not interfere with the process, are useful at the temperatures and pressures envisioned or required by the solvents and temperatures utilized and do not provide residues at levels which are harmful for human consumption.

Applicants herewith submit Examples of the process of the present invention. However, Applicants do not intend to be bound or limited to the materials, temperatures and pressures exemplified.

EXAMPLES

Example 1

CSS (313 grams) was mixed with 625 grams of water and stirred for one (1) hour at room temperature. The mixture was transferred to a four (4) liter separation funnel and shaken with three (3) successive 1200 gram portions of ethyl acetate for 2 minutes each. The organic phases were combined and the solvent evaporated. The residue was dried in a vacuum oven overnight at 95° C. and 30 inch Hg vacuum to provide a pasty solid product.

TABLE 1

| Sample | Weight Grams | Percent Isoflavone Values | Percent Isoflavone Values Recovered |
|---|---|---|---|
| CSS:H₂O | 900.3 | 0.32 | |
| Product | 5.49 | 29.2 | 55 |

Example 2

An amount of 298.1 grams of a mixture, 1:2 weight ratio of CSS and water was prepared. The mixture was contacted with six (6) individual 300 gram portions of ethyl acetate for 1½ hours each. The organic phases were separated from the aqueous phase after each contact and were maintained separately and not mixed. The solvent was evaporated from the six individual extracts recovered and finally the six samples were dried overnight in a vacuum oven at 110° C. and 30 inches Hg vacuum. The six samples were analyzed for isoflavone value content as shown in Table 2.

TABLE 2

| Sample | Weight Grams | Percent Isoflavone Values | Percent Yield Isoflavone Values | Cumulative Percent Yield |
|---|---|---|---|---|
| CSS:Water (1:2) | 298.1 | 0.30 | | |
| Extract 1 Product | 0.92 | 24.1 | 24.6 | 24.6 |
| Extract 2 Product | 0.34 | 33.86 | 12.9 | 37.7 |
| Extract 3 Product | 0.27 | 30.22 | 9.2 | 46.9 |
| Extract 4 Product | 0.25 | 22.79 | 6.4 | 53.2 |
| Extract 5 Product | 0.20 | 19.14 | 4.3 | 57.5 |
| Extract 6 Product | 0.17 | 18.89 | 3.6 | 61.1 |
| Aqueous Phase After 6th Extraction | 242.4 | 0.14 | | |

The data shows that the yield of isoflavone values can be improved by multiple extractions; however, the amount of isoflavone values recovered in each extraction decreases. The isoflavone recovery substantially doubled with three extractions compared to the recovery in a single extraction.

Example 3

In this example the effect of the ratio of CSS to water on the yield and the purity of the isoflavone values was determined. The procedure of Example 1 was followed except that the amount of water was varied and the mixture of CSS:water was contacted three times for two (2) minutes with ethyl acetate in a ratio of four parts ethyl acetate to one part CSS. The three extracts were combined and the extracts evaporated as in Example 1. The experimental results are shown in Table 3.

TABLE 3

| CSS:Water:Ethyl Acetate Parts by Weight | | | Percent Isoflavone Values In Product | Percent Yield Isoflavone Values |
|---|---|---|---|---|
| CSS | Water | Ethyl Acetate | | |
| 1 | 1 | 12 | 23.3 | 59.2 |
| 1 | 1.5 | 12 | 27.6 | 54.8 |
| 1 | 1.5 | 12 | 27.1 | 53.8 |
| 1 | 1.5 | 12 | 28.5 | 55.3 |
| | Average | | 27.7 | 54.6 |
| 1 | 2 | 12 | 26.8 | 46.4 |
| 1 | 2 | 12 | 29.2 | 55. |
| | Average | | 28.0 | 50.7 |
| 1 | 3 | 12 | 28.7 | 50.8 |
| 1 | 3 | 12 | 29.3 | 51.4 |
| 1 | 3 | 12 | 30 | 52.5 |
| | Average | | 29.3 | 51 |

The higher ratio of water to CSS provides a product having a higher concentration of isoflavone values. The lower ratio of water to CSS provides for a higher recovery of isoflavone values from the plant material.

Example 4

In this example, the isoflavone values are recovered from the organic phase extract by addition of a nonsolvent for the isoflavone values in the organic phase. An amount of 150.79 grams of a mixture of CSS and water in a weight ratio of 1:2 was prepared. The 150.7 grams of aqueous mixture was extracted by stirring with 304.2 grams of ethyl acetate for one and a half (1 ½) hours at room temperature. An organic phase of 294.4 grams was recovered and mixed with 79.8 grams of hexane. The ethyl acetate solution became cloudy immediately upon addition of the hexane and a white precipitate formed. In addition a hexane insoluble liquid separated which was presumed to be water. The mixture was maintained at 4° C. overnight and the white precipitate collected by filtration. The filtrate was evaporated to form an extract residue.

TABLE 4

| Sample | Weight Grams | Percent Isoflavone Values | Percent Isoflavone Value Yield |
|---|---|---|---|
| CSS:Water (1:2) | 150.7 | 0.42 | |
| Precipitate | 0.13 | 90.7 | 18.6 |
| Extract Residue | 0.6 | 6.1 | 6.8 |

A product containing isoflavone values at a high purity can be obtained by the process. However, a large amount of the isoflavone values remain in the ethyl acetate.

Example 5

A mixture of CSS:water, 600.21 grams, was extracted with three successive 600 gram portions of ethyl acetate for 1½ hours each extraction. The three organic phases were combined and 90% by weight of the sample was evaporated. A fine white precipitate formed, was filtered from the solution and washed with a minimum of cold ethyl acetate and dried.

TABLE 5

| Sample | Weight Grams | Percent Isoflavone Values in Product | Percent Yield |
|---|---|---|---|
| CSS:Water (1:3) | 600.2 | 0.21 | |
| Precipitate | 0.52 | 85.3 | 35.2 |
| Extract after Removal of Precipitate | 1.7 | 2 | 2.7 |

Precipitation by removal of solvent provides a product containing a high concentration of isoflavone values while only a small amount of isoflavone values remains in the mother liquor.

Example 6

In a 1000 ml Erlenmeyer flask CSS (314.9 grams) was mixed with water (473.2 grams) for one hour with a stirring bar. The CSS:$H_2O$ (1:1.5) mixture (750 grams) was transferred to a separating funnel and extracted with three successive 1200 gram portions of ethyl acetate for two minutes each extraction. The three organic phases were combined and evaporated and the residue was dried in a vacuum oven overnight at 95° C. and 30 inches Hg vacuum. The dried extract (5.48 grams) was stirred for 30 minutes in 40 ml of hexane. An additional 10 ml of hexane was used to transfer the mixture to centrifuge tubes, and the mixture centrifuged for 10 minutes. A total of 32 ml of the hexane phase was separated and evaporated. The remaining hexane was evaporated from the recovered solid. Both the hexane wash solvent and the washed residue were dried in a vacuum oven overnight. Table 6 presents the results of the experiment.

TABLE 6

| Sample | Weight Grams | Percent Isoflavone Values | Percent Yield |
|---|---|---|---|
| Dried Extract | 5.66 | 27.6 | 54.8 |
| Hexane Washed Dried Extract | 3.22 | 42.8 | 48.36 |
| Hexane Wash-Dried | 2.23 | 5.7 | 4.5 |

The hexane wash provides selective removal of non-isoflavone value components with only a modest loss in isoflavone values. The product purity in regard to isoflavone values is substantially increased.

Example 7

A CSS:$H_2O$ (1:3) mixture was prepared by stirring 331.9 grams CSS with 998.9 grams water with a stir bar for one (1) hour. In a 4 liter separation funnel, 1300 grams of the CSS:water mixture were shaken with 1445 ml of ethyl acetate for two (2) minutes. Two phases were allowed to form and the organic phase separated from the aqueous phase. the aqueous phase was re-extracted two additional times with 1445 ml portions of fresh ethyl acetate. The three organic phases recovered were combined, evaporated and the extract (product) dried in a vacuum oven at 100° C. and 30 inches Hg vacuum. Thirty five (35) ml of hexane were added to 5.17 grams of extract and the mixture stirred for 30 minutes. The mixture was transferred to a centrifuge with an additional 20 ml of hexane and centrifuged for 10 minutes. Thirty six ml of hexane was separated from the solid and evaporated. The remaining hexane and solid were treated to evaporate the hexane. The residues from the hexane wash and the hexane washed extract were dried overnight at 95° C. and 30 inches Hg vacuum. The results of the experiment are shown in Table 7.

TABLE 7

| Sample | Weight Grams | Percent Isoflavone Values in Product | Percent Isoflavone Recovery |
|---|---|---|---|
| CSS:$H_2O$ (1:3) | 1300 | 0.23 | |
| Unwashed Dried Extract | 5.25 | 29.3 | 51.4 |
| Hexane Washed Dried Extract | 3.3 | 40.0 | 44.2 |
| Hexane Wash Liquid-Dried | 1.76 | 7.3 | 4.3 |

Washing the extract product with hexane substantially increases the isoflavone value concentration (purity) in the extract product with only a small loss in isoflavone values. The residue from the hexane wash liquor can be recovered and returned to the mixing-extraction zone.

Example 8

An experiment was carried out to determine the effect of extraction temperature on the extraction product and the yield of isoflavone values.

A CSS:$H_2O$ (1:3) mixture was prepared by mixing CSS (211.7 grams) and water (636.1 grams) for 30 minutes with a stir bar. 400 grams of the CSS:$H_2O$ (1:3) mixture was extracted at room temperature with three portions (445 ml) of ethyl acetate. The three separated organic phases were mixed, evaporated and dried. A 400 gram portion of the CSS:$H_2O$ (1:3) mixture was heated to 45° C. and extracted with three portions (445 ml) of ethyl acetate heated to 45° C. The three separated organic phases were combined, evaporated and dried. The results of the experiments are presented in Table 8.

TABLE 8

| Sample | Weight Grams | Percent Isoflavone Values | Percent Yield |
|---|---|---|---|
| CSS:$H_2O$ (1:3) | 400 | 0.23 | |
| Dried Extract Room Temperature | 1.61 | 30.0 | 52.5 |
| Dried Extract 45° C. | 2.18 | 23.7 | 56.2 |

The extract product from the extraction done at room temperature contained a higher concentration of isoflavone values (more pure). The extract from the extraction done at 45° C. was less pure but provided a greater recovery of isoflavone values from the CSS.

Example 9

An experiment was conducted to determine the affect of the addition of a water soluble solvent to the water immiscible solvent.

A CSS:$H_2O$ (1:3) mixture was prepared by mixing 316.2 grams of CSS and 949.6 grams $H_2O$ with a stirring bar for one hour. A 1200 gram portion of the CSS:$H_2O$ (1:3) mixture was transferred to a four liter separating funnel and extracted with three 1360 ml portions of 10% by volume ethanol in ethyl acetate by shaking for two minutes followed by separation of the organic phase. The three separated organic phases were combined, the solvent evaporated and the recovered extract product was dried overnight in a vacuum oven at 95° C. and 30 inches Hg vacuum. The recovered extract product was mixed with 100 ml of hexane for 30 minutes. The mixture was separated by centrifuging and the supernatant hexane layer was removed in increments until the hexane and solid weighed about 15 grams. The hexane was evaporated from the extract and the extract dried overnight at 95° C. and 30 inches Hg vacuum. The hexane wash removed from the extract in increments was evaporated and dried under the same conditions as the extract. the results of the experiment are shown in Table 9.

TABLE 9

| Sample | Weight Grams | Percent Isoflavone Values | Percent Isoflavone Value Yield |
|---|---|---|---|
| CSS:H$_2$O (1:3) | 1200 | 0.23 | |
| Dried Unwashed Extract | 18.3 | 10.9 | 72.3 |
| Dried Hexane Washed Extract | 3.47 | 37.5 | 47.1 |
| Hexane Wash Liquid | 14.47 | 4.0 | 21 |

Example 10

This experiment was done to determine the effect of the pH at which the extraction is done.

CSS (21.97 grams) was mixed with 21.97 grams of 0.5N HCl. The pH of the mixture was 3. A second portion of CSS (15.72 grams) was mixed with 15.72 grams of water and 0.2 grams of 50% NaOH. The pH of the resulting mixture was 9. A 5 gram sample of each of the acidic and basic mixtures was contacted with 5 grams of ethyl acetate. Each mixture was centrifuged and the organic phase recovered and analyzed for isoflavone value content and isoflavone value distribution. Table 10 shows the effect of the pH on the extraction.

As shown in Table 10, the amount of isoflavone values extracted at an alkaline pH is much lower than the amount extracted at an acid pH.

TABLE 10

| pH | Isoflavone Values in CSS grams | Isoflavone Values in Ethyl Acetate grams/gram | Isoflavone Values Extracted grams | Percent Isoflavone Values Recovered |
|---|---|---|---|---|
| 3 | 0.025 | 0.00172 | 0.0086 | 34.4 |
| 9 | 0.025 | 0.000475 | 0.002375 | 9.5 |

The distribution of the isoflavone values in solution in the ethyl acetate organic phase was determined by liquid chromatography. The results are shown in Table 11.

TABLE 11

| pH Phase | 3 Ethyl Acetate | 9 Ethyl Acetate | CSS |
|---|---|---|---|
| Percent Daidzin | 19.71 | 17.59 | 28.08 |
| Percent Glycitin | 0.00 | 0.00 | 0.77 |
| Percent Genistin | 35.98 | 38.58 | 41.42 |
| Percent Mal. Daidzin | 3.88 | 0.24 | 4.56 |
| Percent Mal. Glycitin | 1.70 | 0.00 | 2.52 |
| Percent Mal. Genistein | 19.14 | 5.46 | 13.05 |
| Percent Daidzein | 2.93 | 8.10 | 3.29 |
| Percent Genistein | 3.29 | 9.99 | 0.92 |

The data in Table 11 shows that the distribution of isoflavone values in the extract obtained by extraction at an acid pH more closely approaches the distribution of isoflavone values in the CSS feed.

Several of the extracts from the examples and three different batches of CSS were analyzed by liquid chromatography to determine the total concentration of isoflavone values and the distribution of the individual components which make up the isoflavone values. The results of the analysis are shown in Table 12.

TABLE 12

| Material | Isoflavone Component, Percent by Weight | | | | | | | | Percent by Weight |
|---|---|---|---|---|---|---|---|---|---|
| | Daidzin | Glycitin | Genistin | Malonyl Daidzin | Malonyl Glycitin | Malonyl Genistin | Daidzein | Genistein | Total Isoflavone |
| CSS Lot A | 0.246 | 0.02 | 0.356 | 0.059 | 0.026 | 0.161 | 0.007 | 0.01 | 0.89 |
| CSS Lot B | 0.374 | 0.011 | 0.573 | 0.081 | 0.12 | 0.208 | 0.006 | 0.008 | 1.27 |
| CSS Lot C | 0.287 | 0.016 | 0.415 | 0.059 | 0.01 | 0.162 | 0.004 | 0.005 | 0.96 |
| Extract Source | | | | | | | | | |
| Extract from Example 3 CSS:H$_2$O = 1:1 | 6.37 | 0.42 | 14.69 | 0.16 | 0.05 | 1.22 | 0.19 | 0.2 | 23.3 |
| Extract from Example 3 CSS:H$_2$O = 1:1.5 | 7.36 | 0.49 | 17.48 | 0.17 | 0.13 | 1.47 | 0.24 | 0.27 | 27.6 |
| Extract from Example 3 CSS:H$_2$O = 1:2 | 7.37 | 0.49 | 18.78 | 0.23 | 0.17 | 1.64 | 0.28 | 0.28 | 29.2 |
| Extract from Example 3 CSS:H$_2$O = 1:3 | 6.94 | 0.29 | 19.81 | | | 1.61 | 0.28 | 0.34 | 29.3 |
| Precipitate from Example 4 Hexane as Nonsolvent | 20.7 | 0.64 | 68.4 | | | 0.72 | 0.03 | 0.2 | 90.7 |
| Precipitate from Example 5 Partial Evaporation of Solvent | 19.27 | 0.76 | 64.56 | | | 0.71 | | | 85.3 |
| Dried Extract from Example 6 After hexane wash | 11.35 | 0.74 | 28.52 | 0.19 | 0.07 | 1.44 | 0.25 | 0.24 | 42.8 |
| Dried Extract from Example 7 After hexane wash | 9.3 | 0.36 | 27.97 | | | 1.74 | 0.3 | 0.35 | 40 |
| Dried Extract from Example 8 Extraction at 45° C. | 6.04 | 0.29 | 15.77 | | | 1.18 | 0.2 | 0.26 | 23.7 |

TABLE 12-continued

| Material | Isoflavone Component, Percent by Weight | | | | | | | | Percent by Weight |
|---|---|---|---|---|---|---|---|---|---|
| | Daidzin | Glycitin | Genistin | Malonyl Daidzin | Malonyl Glycitin | Malonyl Genistin | Daidzein | Genistein | Total Isoflavone |
| Dried Extract from Example 9 From 10% EtOH in EtOA$_c$, Before hexane wash | 3.6 | 0.18 | 6.4 | | | 0.56 | 0.08 | 0.1 | 10.9 |
| Dried Extract from Example 9 From 10% EtOH in EtOA$_c$, After hexane wash | 8.95 | 0.33 | 27.35 | | | 0.59 | 0.09 | 0.19 | 37 |

The analysis presented in Table 12 shows the improvement in isoflavone value concentration (purity) which can be obtained by the process of the invention.

Alkyl acetate is a preferred solvent due to its unexpected selectivity for isoflavone values in the presence of saccharides and protein in the biomass from which the isoflavone values are extracted. In addition ethyl acetate extracts the various forms of the isoflavone values from the biomass in a proportion close to that at which the various individual isoflavones are present in the mixture.

Experiments were carried out to determine the efficiency of extraction of isoflavone values in various solvents. The results of the experiments are shown in Table 13.

TABLE 13

Solvent Extraction of Isoflavone Values from CSS

| Solvent | % Isoflavone Recovered in Solvent |
|---|---|
| Acetone | 51 |
| Acetic Acid | 51 |
| Methanol | 43 |
| Ethyl Acetate | 24 |
| Methyl Isobutyl Ketone | 18 |
| CYANEX 923 | <1 |
| CYANEX 921 | <1 |
| Alumine 336 | <1 |

An experiment was carried out to determine the selectivity of various solvents for isoflavone values in CSS. The CSS was diluted with 50% by weight of water and extracted with five different solvents. The amounts of isoflavones and other organic materials extracted were measured. The results of the experiment are shown in Table 14.

TABLE 14

Solvent Extraction: CSS

| Sample | 55-3 | 55-2 | 78-2 | 78-4 | 78-3 |
|---|---|---|---|---|---|
| Solvent | MeOH | EtOAC | Acetone | Acetic Acid | Methyl Isobutyl Ketone |
| CSS Diluent | H2O | H2O | H2O | H2O | H2O |
| % ISFV in Org Phase | 0.23 | 0.10 | 0.24 | 0.24 | 0.05 |
| % Other Materials in Org Phase | 11.57 | 0.14 | 6.83 | 13.26 | 1.74 |
| Others: ISFV | 50.3 | 1.4 | 28.5 | 55.3 | 34.8 |
| % Selectivity to ISFV | 1.9 | 41.7 | 3.4 | 1.8 | 2.8 |
| % of ISFV in CSS Extracted | 44.8 | 19.5 | 48.8 | 48.8 | 10.2 |

The result of the experiment shows that although ethyl acetate extracted a smaller percentage of isoflavone values from the CSS, it had a selectivity far higher than any of the other solvents tested. Even though ethyl acetate extracted only 19.5% of the isoflavone values in the CSS, the organic phase contained only 0.14% of other extracted materials to provide a selectivity of 41.7% toward isoflavone values. That is, out of one gram of isoflavone values in the CSS, 0.19 grams were extracted into the ethyl acetate along with 0.27 grams of other material. For comparison consider acetone, the next most selective solvent. Out of 1 gram of isoflavone values in the CSS, 0.48 grams would be extracted into the acetone, but 13.7 grams of other materials would also be extracted making it difficult to obtain a product with a high isoflavone content. The selectivity of ethyl acetate is considerably higher than any of the other solvents tested. The selectivity makes the extracted material easier to purify to provide a product containing a high concentration of isoflavone values. The percent selectivity is calculated by dividing the % isoflavone values in the organic phase by the sum of the % isoflavone values and the % of other materials in the organic phase and multiplying by 100. Cyclohexanol and methyl acetate are also selective solvents but not as effective and selective as ethyl acetate. The selectivity of the solvent is preferably at least about 10%, more preferably at least about 20% and most preferably at least about 30%.

An experiment was carried out to determine the effect of addition of water to the nonsolvent contacting liquid in the solid washing stage of the process. An extract of CSS was evaporated to obtain a residue containing 40% to 50% solids. The residue was contacted with a mixture of hexane and varying amounts of water. The isoflavone values were separated from the solvent mixture by centrifuge or filtration. The recovered solids were oven dried and analyzed for isoflavone value content.

FIG. 9 is a plot showing the purity of the isoflavone product versus the amount of water in the hexane. As shown in FIG. 9, a small amount of water substantially increases the isoflavone content of the product. As little as about 0.5% by weight water in the hexane resulted in an almost 100% increase in the content of isoflavone values in the product. About 2% by weight water in the hexane increased the content of isoflavone value in the product from 14% by weight to 40% by weight. Additional amounts of water increased the content of isoflavone values in the product still further.

A few runs were made wherein the product was washed a second time with hexane not containing water. The results of the experiment are shown with the square marks. As can be seen, the second wash did not substantially increase the purity of the product. The best results were obtained by adjusting the hexane water mixture for a single wash.

The present process can recover isoflavone values from plant starting material in high yield to provide an isoflavone product containing more than 30% by weight isoflavone values.

What is claimed is:

1. A process for recovering isoflavone values from a plant material containing isoflavone values which comprises:
   a) Extracting the isoflavone values from the plant material by contacting the plant material with a selective solvent for the isoflavone values to form a solution of the isoflavone values in the solvent;
   b) Separating the solution of the isoflavone values from the undissolved plant material;
   c) Separating at least a portion of the isoflavone values from the solvent to form a mixture comprising solid isoflavone values; and
   d) Contacting the mixture comprising solid isoflavone values with a solvent for impurities in the mixture to provide a dried product containing at least about 30% isoflavone values by weight.

2. The process of claim 1 wherein the isoflavone values are extracted from a mixture of the plant material and water by contact with the selective solvent which is immiscible with water, wherein the ratio by weight of the plant material, on a dry solids basis, to the water is from about 1:1 to about 1:15.

3. The process of claim 2 wherein the selective solvent is ethyl acetate.

4. The process of claim 1 wherein the ratio by weight of plant material to selective solvent is from about 1:0.5 to about 1:20.

5. The process of claim 1 wherein the isoflavone value solids are formed from the selective solvent by at least one method selected from the group consisting of evaporation of the solvent, crystallization and precipitation by addition of a nonsolvent for the isoflavone values to the solution of the isoflavone values in the selective solvent.

6. The process of claim 5 wherein the isoflavone values which are separated from the selective solvent are contacted with a solvent in which the isoflavone values have a low solubility and which is miscible with the selective solvent.

7. The process of claim 6 wherein the solvent in which the isoflavone values have a low solubility is a non-polar solvent.

8. The process of claim 7 wherein the non-polar solvent is selected from the group consisting of pentane, hexane, heptane, octane, their isomers and mixtures thereof.

9. The process of claim 6 wherein the solvent in which the isoflavone values have a low solubility is mixed with about 0.5 to about 20% by weight of the solvent with water.

10. The process of claim 9 wherein the mixture comprising solid isoflavone values comprises the selective solvent and solid isoflavone values.

11. The process of claim 10 wherein the solvent in which the isoflavone values have a low solubility comprises a non-polar solvent.

12. The process of claim 1 wherein the selective solvent has a selectivity of at least about 10%.

13. The process of claim 1 wherein the mixture comprising solid isoflavone values is contacted with a nonsolvent for the isoflavone values which is miscible with the selective solvent.

14. The process of claim 13 wherein the nonsolvent for the isoflavone values is a non-polar solvent.

15. The process of claim 14 wherein the nonsolvent for the isoflavone values comprises a non-polar solvent and from about 0.5% to about 20% by weight of the solvent of water.

16. A process for recovering isoflavone values from a plant material which comprises:
   a) Extracting isoflavone values from the plant material by contacting a mixture of the plant material and water with a selective organic solvent for the isoflavone values which is immiscible with water to form a solution of the isoflavone values in the organic solvent and an extracted aqueous phase;
   b) Separating the solution of the isoflavone values in the organic solvent from the extracted aqueous phase;
   c) Separating at least a portion of the organic solvent from the isoflavone values to produce a mixture comprising solid extracted product;
   d) Contacting the mixture comprising the solid extracted product with a solvent for impurities in the mixture comprising the solid extracted product to provide a washed extracted product; and
   e) Removing the solvent from the washed extracted product.

17. The process of claim 16 wherein the selective organic solvent is ethyl acetate.

18. The process of claim 16 wherein the solvent for impurities in the extracted product is a non-polar liquid which is miscible with the selective solvent.

19. The process of claim 18 wherein the solvent for impurities in the extracted product is a liquid hydrocarbon selected from the group consisting of pentane, hexane, heptane, octane, their isomers and mixtures thereof.

20. The process of claim 16 wherein the mixture comprising the solid extracted product comprises a mixture of isoflavone value solids with the selective solvent.

21. The process of claim 16 wherein the mixture comprising the solid extracted product comprises dried isoflavone value solids.

22. The process of claim 16 wherein the solvent for impurities in the mixture comprising the solid extracted product comprises a mixture comprising a non-polar solvent and from about 0.5% to about 20% by weight of the mixture of water.

23. The process of claim 16 wherein the selective solvent is ethyl acetate and the ratio by weight of ethyl acetate to the plant material to be extracted is from about 1:1 to about 30:1.

24. The process of claim 16 wherein the ratio of solvent for the impurities in the isoflavone values to the solid isoflavone values is from about 0.5:1 to about 20:1.

25. The process of claim 16 wherein the selective solvent has a selectivity of at least about 10%.

26. In a process for recovering isoflavone values from a biomass wherein the isoflavone values are extracted from the biomass to form an extract and the isoflavone values are recovered from the extract, the improvement which comprises contacting the recovered isoflavone values with a nonsolvent or antisolvent for the isoflavone values in admixture with from about 0.5% to about 20% by weight based on the nonsolvent or antisolvent of water.

27. The process of claim 26 wherein a slurry of isoflavone values in the extracting solvent is contacted with the admixture of the nonsolvent or antisolvent and water.

28. The process of claim 26 wherein isoflavone values which have been separated from the extracting solvent are contacted with the admixture of nonsolvent or antisolvent and water.

* * * * *